United States Patent [19]
Holder

[11] Patent Number: 4,571,000
[45] Date of Patent: Feb. 18, 1986

[54] VEST TYPE RESTRAINING GARMENT

[76] Inventor: Ocie S. Holder, 302 Witten La., Gastonia, N.C. 28052

[21] Appl. No.: 618,237

[22] Filed: Jun. 7, 1984

[51] Int. Cl.⁴ ............................................. A47C 31/00
[52] U.S. Cl. ..................................... 297/465; 128/134
[58] Field of Search ........................ 128/134; 297/465

[56] References Cited
U.S. PATENT DOCUMENTS

| | | |
|---|---|---|
| 2,449,741 | 9/1948 | Fitzpatrick ...................... 297/465 X |
| 2,782,783 | 2/1957 | Gay . |
| 2,827,898 | 3/1958 | Thompson . |
| 2,908,324 | 10/1959 | Muller et al. ......................... 297/465 |
| 3,099,486 | 7/1963 | Scott ..................................... 297/465 |
| 3,181,530 | 5/1965 | Storey ............................... 297/465 X |
| 3,276,432 | 10/1966 | Murcott . |
| 3,502,073 | 3/1970 | Stanley ................................. 126/134 |
| 3,788,309 | 1/1974 | Zeilman . |
| 3,897,778 | 8/1975 | Forbes-Robinson et al. . |
| 4,132,230 | 1/1979 | Ladd . |
| 4,143,914 | 3/1979 | Klich ..................................... 297/465 |
| 4,360,014 | 11/1982 | Manahan . |

Primary Examiner—James T. McCall
Attorney, Agent, or Firm—Bell, Seltzer, Park & Gibson

[57] ABSTRACT

A vest type restraining garment is disclosed, which is generally in the form of a rectangular sheet, and which includes an opening in a medial location to define front and rear panels. The head of the wearer is adapted to be received through the opening and the front and rear panels overlie the chest and back of the wearer, respectively. A flexible strap is attached to the front panel and includes free end portions extending outwardly from each corner thereof, and a pair of interconnecting rings are mounted to the back panel, with one of the interconnecting rings being located adjacent each corner thereof. These interconnecting rings are adapted to receive respective ones of said free end portions of said tie means therethrough, and so that the end portions of the tie means may then be secured to a chair, bed, or the like. A piece of elastic extends along the end edge of the back panel between the interconnecting rings and serves to form a gathered edge for conforming the sheet to the body of the wearer and preventing riding up of the garment.

10 Claims, 7 Drawing Figures

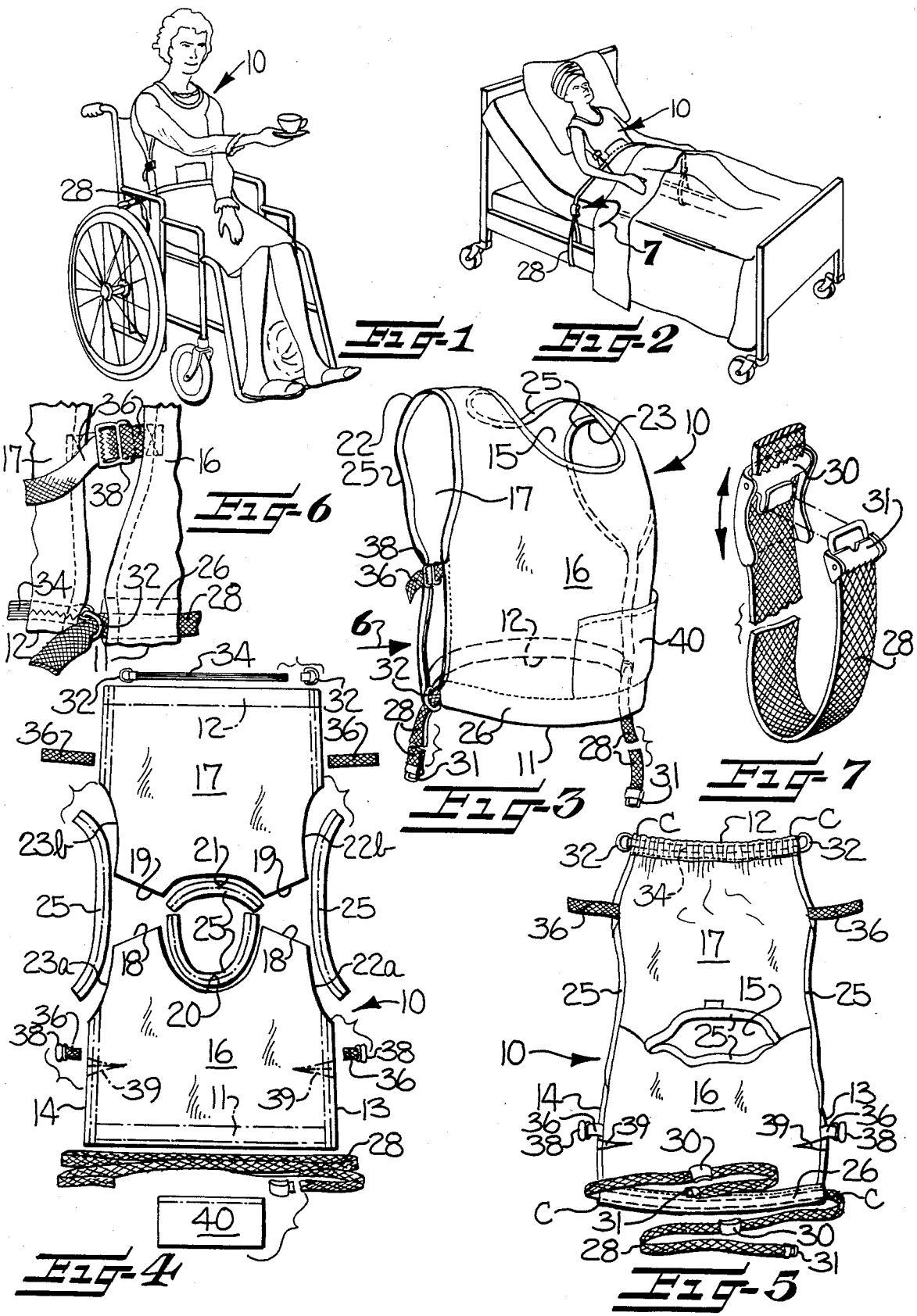

VEST TYPE RESTRAINING GARMENT

FIELD OF THE INVENTION

This invention relates generally to restraining garments of the type which are used to restrain an elderly or invalid person to a bed, wheelchair or the like.

DESCRIPTION OF THE PRIOR ART

Confining or restraining garments and devices are well known in the art. Devices of this type are generally employed by medical or supervisory personnel upon the necessity of confining an infirmed individual to a wheelchair, bed, chair or other suitable structure. Persons in need of restraint encompass the entire age spectrum and include those not in full control of their motor functions, as a result of any one of a variety of causes.

A great number of restraining garments are currently available. However, they typically exhibit one or more of a number of deficiencies which include, lack of comfort, potential for development of bed sores and skin chafing resulting from extended wear, and lack of patient acceptance.

Of the above mentioned deficiencies, the most serious flaws are lack of comfort in combination with the related problems of chafing/bed sores. Many of the garments available in the market have as their primary function, the restraint of the wearer. As a result, little thought is given to the wearer's comfort or even the possibility of injury during use.

In general, patients need only to be confined to a supporting structure to prevent the injuries which occur as a result of falling out of a bed, wheelchair, etc. It is unnecessary to restrict the patient's movements beyond the point of confinement to the supporting structure.

Unfortunately, existing restraining garments have not been designed to allow patients a limited range of motion, while still maintaining effective restraint. The natural tendency of many wearers is to twist, turn, wriggle, lean forward, etc. while wearing the garment. As a consequence of this natural tendency to move about, the wearer will develop bed sores if the garment is not properly designed and fitted. Also, certain of the present types of restraining garments tend to tightly cinch about the waist of the wearer, thereby further aggravating the discomfort of the wearer, and possibly contributing to circulatory problems.

It is accordingly an object of the present invention to provide a restraining garment which overcomes the above noted problems associated with the prior art devices, and which is comfortable.

It is a further object to provide a restraining garment which avoids undue cinching about the waist of the wearer, and which may be worn for extended periods of time without the development of bed sores or chafed skin caused as a result of friction or "riding up" of the garment.

More particularly, it is an object to provide a restraining garment having conformability and giveability, and which allows the wearer a limited range of motion without tending to develop bed sores.

Another object is to provide a garment with increased patient acceptance by incorporating a design which approximates a vest.

SUMMARY OF THE INVENTION

In accordance with the present invention, there is provided a restraining garment for securing a person to a bed, chair or other supporting structure, and which is characterized by the ability to closely conform to the body of the wearer so as to effectively and comfortably hold the wearer in place without undue cinching about the waist. The garment takes the shape of a generally rectangular sheet of flexible material with side edges and end edges, and the sheet includes an opening in a medial location to define front and rear panels on opposite sides of the opening. The sheet may thus be positioned on a wearer, with the wearer's head extending through the opening, and the front and rear panels respectively overlying the chest and back of the wearer. A flexible strap is supported by the front panel and includes free end portions extending outwardly from each corner thereof. A pair of interconnecting means is mounted to the back panel, with one of the interconnecting means being located adjacent each corner thereof. These interconnecting means are adapted to engage a respective one of said free end portions of said tie means. In addition, a piece of elastic extends along the end edge of the back panel between the interconnecting means and serves to form a gathered edge for conforming the sheet to the body of the wearer and for preventing riding up of the garment.

BRIEF DESCRIPTION OF THE DRAWINGS

Some of the objects of the invention having been stated, other objects will appear as the description proceeds when taken on connection with accompanying drawings in which:

FIG. 1 is a perspective view of a wheelchair having a patient sitting therein and secured thereto by a vest restraining garment which embodies the features of the present invention;

FIG. 2 is a perspective view of a bed having a patient lying therein and secured thereto by the vest restraining garment of the present invention;

FIG. 3 is a perspective view of the vest restraining garment in its configuration while being worn by a patient;

FIG. 4 is an exploded top view of the vest restraining garment viewed in a flattened condition from the inside;

FIG. 5 is a top view of the vest restraining garment viewed in a flattened condition from the inside;

FIG. 6 is an enlarged fragmentary side view of the vest restraining garment viewed in the direction of arrow 6 of FIG. 3; and FIG. 7 is a partial perspective view of the elongate tie means of the garment.

DETAILED DESCRIPTION OF THE PREFERRED EMBODIMENT

Referring more particularly to the drawings, a restraining garment which embodies the features of the present invention is indicated generally at 10. The garment 10 is adapted to cover the upper portion of the wearer's body, and it is effective to restrain a patient to a variety of supporting structures, such as a wheelchair or a bed as illustrated in FIGS. 1 and 2.

Referring now to FIGS. 3 through 7, the restraining garment 10 is therein disclosed in detail. FIG. 3 illustrates the general shape of the garment as it would appear while being worn by a patient. When viewed in a flattened condition as seen in FIG. 5, the garment 10 takes the form of a generally rectangular elongate sheet of flexible material. The generally rectangular sheet has opposite end edges 11 and 12, and opposite side edges 13 and 14, and defines a corner C at each junction of the side and end edges. The sheet further includes an opening 15 in a medial location to define front and rear panels 16 and 17 respectively on opposite sides of the opening 15 so that the sheet is adapted to be positioned on a wearer with the wearer's head extending through the opening and with the front and rear panels respectively overlying the chest and back of the wearer, note FIGS. 1–3.

As illustrated in FIG. 4, the front and rear panels 16 and 17 are formed from separate pieces of fabric material, such as woven cotton fabric, which are sewn together along a pair of contiguous edges 18 and 19 respectively, on each side of the opening 15. Also, it will be seen that the opening 15 is defined by mating arcuately curved sections 20 and 21 of the mating ends of the pieces, and each pair of the mating edges 18 and 19 are cut so as to be inclined with respect to each other, and with respect to the widthwise direction as represented by the end edges 11 and 12 of the finished sheet 10. The edges 18 and 19 thus shape the portions of the sheet on each side of the opening 15 into an arcuate configuration as seen in FIG. 3 which is adapted to smoothly overlie the shoulders of the wearer.

As seen in FIGS. 3 and 4, the opposite sides 13 and 14 of the sheet each include an arcuately and inwardly curved medial portion 22, 23 respectively, with each such curved portion consisting of a curved segment in each panel. In particular, the curved portion 22 on the side edge 13 comprises the curved segment 22a on the panel 16 and a mating curved segment 22b on the panel 17. The curved portion 23 on the side edge 14 comprises the segments 23a and 23b. The curved portions 22, 23 each have an overall length equaling about one half the longitudinal length of the sheet, and each extends inwardly toward the opening 15 so as to reduce the width of that portion of the garment which is adapted to overlie the shoulders of the wearer, to better define openings for the arms of the wearer. The head opening 15 and the curved portions 22, 23 for the arm openings are each lined with soft fabric edging 25, such as woven cotton, in order to prevent skin chafing and to provide a more finished appearance.

The garment 10 further comprises a hem 26 which is formed along the end edge 11 of the front panel. A flexible elongate tie means 28 in the form of a webbed strap having a medial portion and oppositely extending end portions is also provided, which is slideably received in the hem 26. Attached to each end of the tie means is a conventional buckle 30 and mating clasp 31.

A pair of ring means in the form of metal D-rings 32 are mounted to each corner of the rear panel 12. Also, mounted between the respective corners is an elastic means 34. This elastic means, in the form of a strip of elastic, is sewn in its stretched state to the back panel and extends along substantially the entire length of the end edge 12 thereof. A gathered end edge is thereby formed when the tension on the elastic strip is released. Strap means 36, 37 are provided which are attached to the medial portions of the side edges of each panel. Connected to each end of those straps 36 which are attached to the front panel 16 are conventional frictionally engaging fasteners or buckles 38. In addition, optional darts 39 and a utility pocket 40 may be included on the front panel.

The complete garment 10 as depicted in FIG. 5 is designed to be positioned on a wearer with the wearer's head extending through the medially located opening 15 so that the front and rear panels overlie the chest and back of the wearer, respectively. Upon the tapered edges 18 and 19 adjacent the medially located opening being sewn together, the garment will be adapted to be shaped into the configuration shown in FIG. 3, with the portions on opposite sides of the opening 15 adapted to smoothly overlie the shoulders of the wearer.

The medial portion of the flexible elongate tie means 28 is slideably mounted in hem 26. When placed on the wearer, the respective ends of the tie means 28 are threaded through the aforementioned rings 32. The tie means 28 may then be looped around the supporting structure and each of the buckle 30 and clasp 31 pairs may be appropriately tightened to secure the wearer in the garment. The strap means 36 are threaded through the frictionally engaging fasteners 38 and are tightened to bring the respective panels into a proximate relation with the wearer so as to prevent the wearer from slipping out of the garment. The elastic strip 34 that is sewn into the end edge 12 of the rear panel serves to prevent chafing of the skin and bed sores by allowing the garment to flex and stretch as the wearer moves, and by resisting upward movement of the end edge on the back of the wearer.

In the drawings and specification, there has been set forth a preferred embodiment of the invention, and although specific terms are employed, they are used in a generic and descriptive sense only and not for purposes of limitation.

That which is claimed is:

1. A garment for securing a person to a bed, chair, or other supporting structure, which is characterized by the ability to closely conform to the body of the wearer so as to effectively and comfortably hold the wearer in place without undue cinching about the waist, and comprising:
   a generally rectangular elongate sheet of flexible material having opposite end edges and opposite side edges, and defining a corner at each junction of the side and end edges, said sheet including an opening in a medial location to define front and rear panels on opposite sides of the opening so that said sheet is adapted to be positioned on a wearer with the wearer's head extending through said opening and with the front and rear panels respectively overlying the chest and back of the wearer;
   flexible elongate tie means supported by one of said panels and including a free end portion extending outwardly from each corner thereof;
   a pair of interconnecting means supported by the other of said panels, with one of said interconnecting means being located adjacent each corner thereof, and with each of said interconnecting means being adapted to engage a respective one of said free end portions of said tie means; and
   elastic means extending along substantially the entire length of said end edge of said other panel and at least substantially between said pair of interconnecting means to form a gathered edge for conforming the sheet to the body of the wearer and resisting the riding up of the sheet.

2. A garment according to claim 1 wherein said elongate tie means comprises a continuous strap and wherein the end edge of said one panel includes a hem slideably receiving the medial portion of said strap therein.

3. A garment according to claim 1 wherein said pair of interconnecting means comprises a pair of rings.

4. A garment according to claim 1 wherein said elastic means is located within a hem.

5. A garment according to claim 1 further comprising a utility pocket attached to said front panel.

6. A garment for securing a person to a bed, chair, or other supporting structure, which is characterized by the ability to closely conform to the body of the wearer so as to effectively and comfortably hold the wearer in place without undue cinching about the waist, and comprising:
- a generally rectangular elongate sheet of flexible material having opposite end edges and opposite side edges, and having a corner at each junction of the side and end edges, said sheet including an opening in a medial location to define front and rear panels on opposite sides of the opening so that said sheet is adapted to be positioned on a wearer with the wearer's head extending through said opening and with the front and rear panels respectively overlying the chest and back of the wearer;
- a hem formed along the end edge of said front panel;
- flexible elongate tie means comprising a medial portion and oppositely extending free end portions, said medial portion slideably positioned in said hem with said free end portions extending outwardly from respective ends thereof;
- a pair of ring means mounted to said back panel, with one of said ring means being located adjacent each corner thereof and being adapted to receive a respective one of said free end portions of said tie means; and
- elastic means extending along substantially the entire length of said end edge of said back panel and between said pair of ring means, to form a gathered edge for conforming the sheet to the body of the wearer and resisting riding up of the garment.

7. A garment according to claim 6 wherein said front and rear panels comprise separate pieces of fabric material which are sewn together along a pair of contiguous edges on each side of said opening, and with each pair of contiguous edges being inclined with respect to the end edges of said sheet so as to form the portions of the sheet on each side of the opening into an arcuate configuration adapted to smoothly overlie the shoulders of the wearer.

8. A garment according to claim 7 wherein each of the opposite sides of said sheet includes an arcuately curved portion extending inwardly toward said opening so as to reduce the width of that portion of the garment which is adapted to overlie the shoulders of the wearer, and thereby define a shoulder opening.

9. A garment as defined in claim 8 wherein the periphery of said opening and the periphery of each of said arcuately curved portions of said opposite sides of said sheet are lined with a soft fabric edging.

10. A garment for securing a person to a bed, chair, or other supporting structure, which is characterized by the ability to closely conform to the body of the wearer so as to effectively and comfortably hold the wearer in place without undue cinching about the waist, and comprising:
- a generally rectangular elongate sheet of flexible material having opposite end edges and opposite side edges, and defining a corner at each junction of the side and end edges, said sheet including an opening in a medial location to define front and rear panels on opposite sides of the opening so that said sheet is adapted to be positioned on a wearer with the wearer's head extending through said opening and with the front and rear panels respectively overlying the chest and back of the wearer;
- strap means mounted to the medial portion of each side edge of each panel, with the two strap means on each side edge of said garment being adapted to interconnect with each other beneath the arms of the wearer,
- flexible elongate tie means supported by one of said panels and including a free end portion extending outwardly from each corner thereof;
- a pair of interconnecting means supported by the other of said panels, with one of said interconnecting means being located adjacent each corner thereof, and with each of said interconnecting means being adapted to engage a respective one of said free end portions of said tie means; and
- elastic means extending along said end edge of said other panel and at least substantially between said pair of interconnecting means to form a gathered edge for conforming the sheet to the body of the wearer and resisting the riding up of the sheet.

* * * * *